United States Patent [19]

Nishiyama et al.

[11] Patent Number: 5,646,244

[45] Date of Patent: Jul. 8, 1997

[54] CYCLODEPSIPEPTIDE COMPOUND

[75] Inventors: Hitoshi Nishiyama, Neyagawa; Masaru Ohgaki, Kobe; Ryo Yamanishi, Ibaraki; Toshihiko Hara, Miho-mura, all of Japan

[73] Assignee: Fujisawa Pharmaceutical Co., Ltd., Osaka, Japan

[21] Appl. No.: 605,064

[22] PCT Filed: Aug. 31, 1994

[86] PCT No.: PCT/JP94/01446

§ 371 Date: Mar. 6, 1996

§ 102(e) Date: Mar. 6, 1996

[87] PCT Pub. No.: WO95/07272

PCT Pub. Date: Mar. 16, 1995

[30] Foreign Application Priority Data

Sep. 6, 1993 [JP] Japan ................... 5-246323

[51] Int. Cl.$^6$ ................... C07K 11/02; A61K 1/395
[52] U.S. Cl. ................... 530/317; 930/30
[58] Field of Search ................... 530/317; 514/11; 930/30

[56] References Cited

U.S. PATENT DOCUMENTS 5,514,773  5/1996  Nishiyama et al. ................... 530/317

FOREIGN PATENT DOCUMENTS 9419334  1/1994  WIPO .

*Primary Examiner*—Howard E. Schain
*Attorney, Agent, or Firm*—Oblon, Spivak, McClelland, Maier & Neustadt, P.C.

[57] ABSTRACT

A compound of the formula:

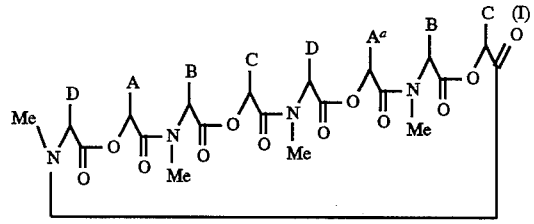

wherein A is benzyl group which has suitable substituent (s), $A^a$, B and D are each lower alkyl, C is hydrogen or lower alkyl, or a salt thereof.

The compound or its salt of the present invention has excellent parasiticidal activities as parasiticides (anthelmintics) for animals and human bodies.

11 Claims, No Drawings

CYCLODEPSIPEPTIDE COMPOUND

TECHNICAL FIELD

The present invention relates to new depsipeptide derivatives having antiparasitic activity.

BACKGROUND ART

Japanese Kokai Tokkyo Koho 3-35796 and 5-170749 disclose depsipeptide derivatives prepared by culturing microorganisms.

As depsipeptide substances having parasiticidal activity, substance PF1022 (Japanese Kokai Tokkyo Koho 3-35,796) and substance PF1022B, substance PF1022C, substance PF1022D (Japanese Kokai Tokkyo Koho 5-170,749) are known, and among these compounds the effectiveness of substance PF1022 on gastrointestinal parasites (whipworms, haemonchus, hairworms and roundworms living in the stomach and intestine) has been confirmed. This time, the object was to find a drug having a stronger effect on gastrointestinal parasites and also effective on tissue parasites (for example filariid worms living in blood vessels, lungworms living in the lungs, liver flukes living in the liver).

DISCLOSURE OF INVENTION

The object compound of the present invention, depsipeptide derivatives (I) can be represented by the following general formula:

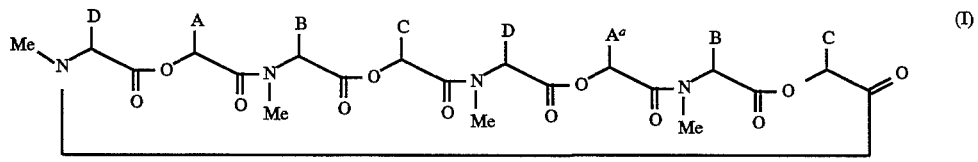

wherein A is benzyl group which has suitable substituent(s),
$A^a$, B and D are each lower alkyl, and
C is hydrogen or lower alkyl.

According to the present invention, the object compound, the depsipeptide derivatives (I) can be prepared by the following processes.

It should be indicated that any of D-configured compound, L-configured compound and/or DL-configured compound are included in the scope of the present invention; however, for the convenience, only D-configured compounds and L-configured compounds are explained in the process for preparation as follows.

Process 1

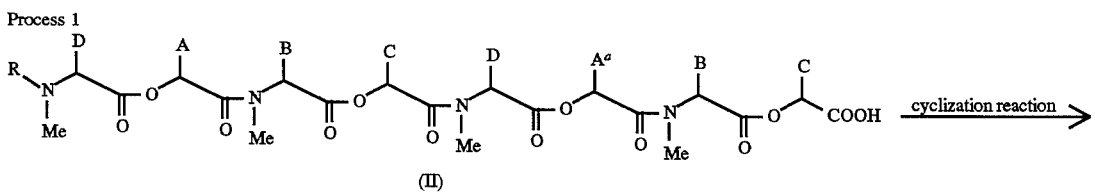

or its reactive derivative at the
amino or carboxy group or a salt thereof

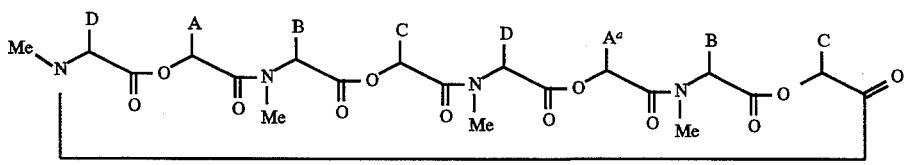

or a salt thereof

Process 2
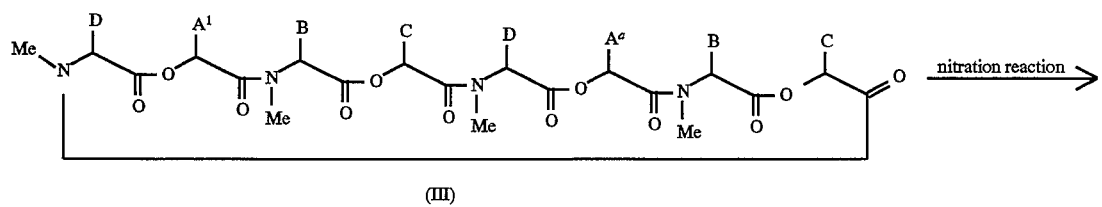
(III)
or a salt thereof
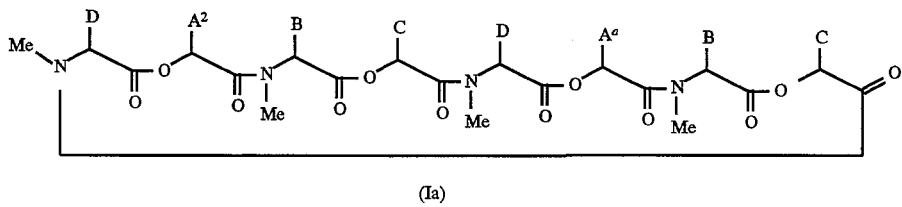
(Ia)
or a salt thereof
Process 3
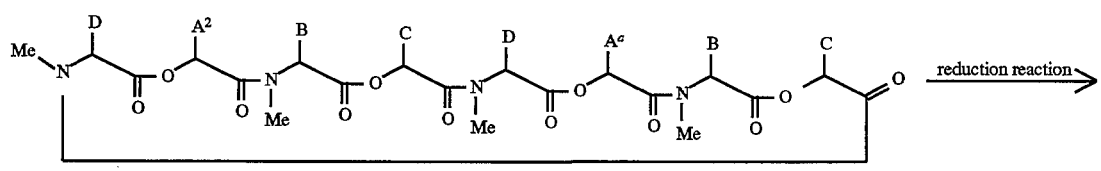
(Ia)
or a salt thereof
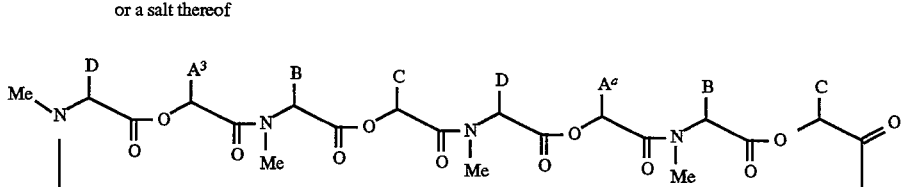
(Ib)
or a salt thereof
Process 4
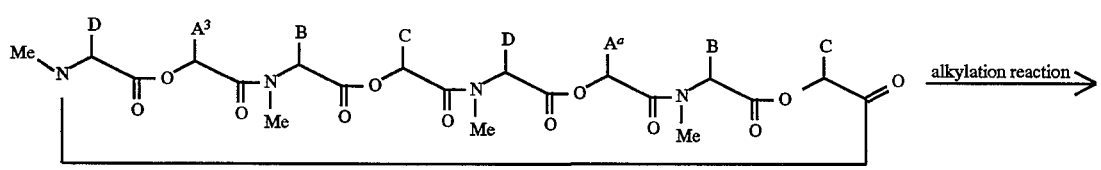
(Ib)
or a salt thereof
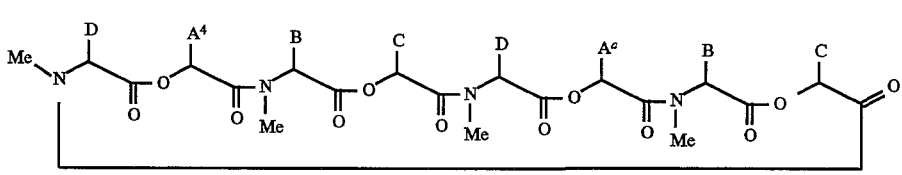
(Ic)
or a salt thereof Process 5
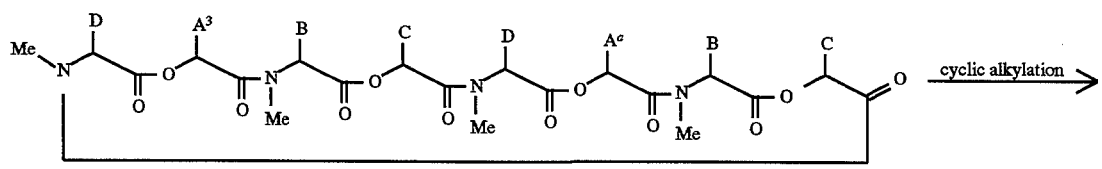
(Ib)
or a salt thereof
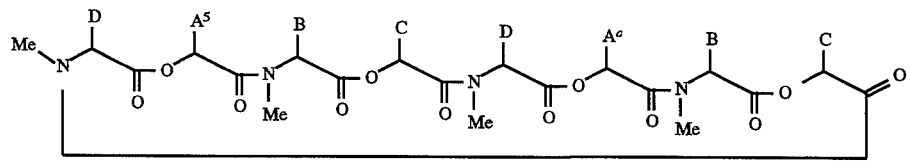
(Id)
or a salt thereof
Process 6
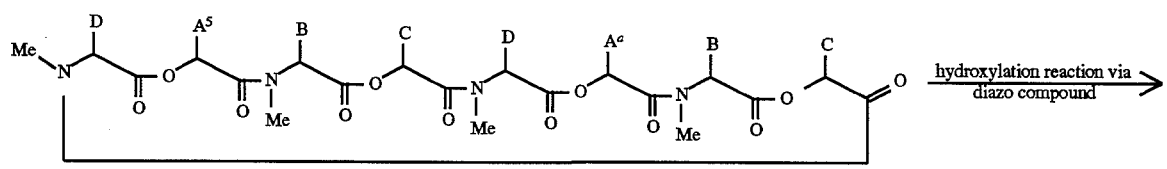
(Ib)
or a salt thereof
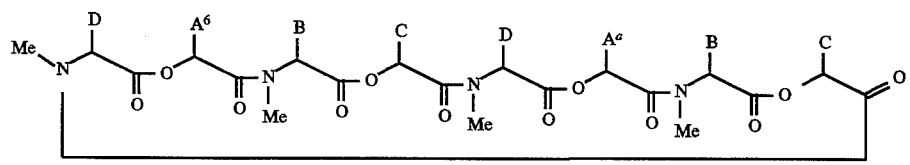
(Ie)
or a salt thereof
Process 7
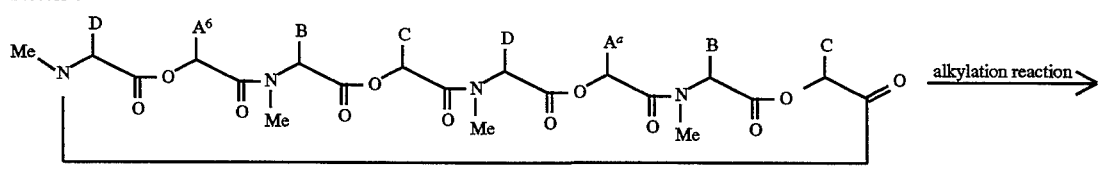
(Ie)
or a salt thereof
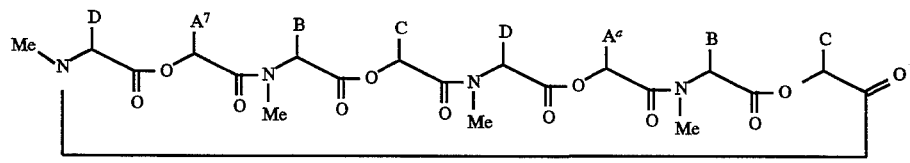
(If)
or a salt thereof Process 8

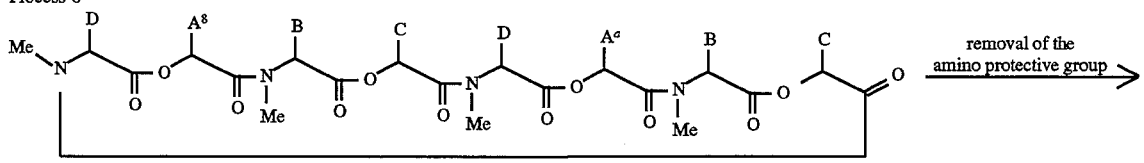

(Ig)

or a salt thereof

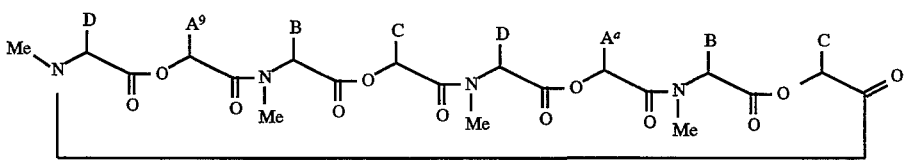

(Ih)

or a salt thereof wherein A, $A^a$, B, C and D are each as defined above,

R is hydrogen or amino protective group, $A^1$ is benzyl group or benzyl group which has lower alkoxy, $A^2$ is benzyl group which has nitro, or benzyl group which has nitro and lower alkoxy, $A^3$ is benzyl group which has amino, or benzyl group which has amino and lower alkoxy, $A^4$ is benzyl group which has mono- or di- lower alkylamino, or benzyl group which has mono- or di- lower alkylamino and lower alkoxy, $A^5$ is benzyl group which has cyclic amino, or benzyl group which has cyclic amino and lower alkoxy, $A^6$ is benzyl group which has hydroxy, or benzyl group which has hydroxy and lower alkoxy, $A^7$ is benzyl group which has lower alkoxy, $A^8$ is benzyl group which has protected amino and $A^9$ is benzyl group which has amino.

Throughout the present specification, the amino acids, peptides, protective groups, condensing agents, etc. are indicated by the abbreviations according to the IUPAC-IUB (Commission on Biological Nomenclature) which are in common use in the field of art.

Moreover, unless otherwise indicated, the amino acids and their residues when shown by such abbreviations are meant to be L-configured compounds and residues, and when shown by D-abbreviations, they are meant to be D-configured compounds and residues.

In the present invention, there are employed the following abbreviations.

p-Me₂NPhLac:3-(4-dimethylaminophenyl)-2-hydroxypropionic acid [β-(p-dimethylaminophenyl)lactic acid]

p-MorPhLac:2-hydroxy-3-(4-morpholinophenyl)propionic acid [β-(p-morpholinophenyl)lactic acid]

p-MeOPhLac:2-hydroxy-3-(4-methoxyphenyl)propionic acid [β-(p-methoxyphenyl)lactic acid]

Lac:2-hydroxypropionic acid [lactic acid]

p-NO₂PhLac:2-hydroxy-3-(4-nitrophenyl)-propionic acid [β-(p-nitrophenyl)lactic acid]

p-NH₂PhLac:3-(4-aminophenyl)-2-hydroxypropionic acid [β-(p-aminophenyl)lactic acid]

p-CbmNHPhLac:2-hydroxy-3-(4-methoxycarbonylaminophenyl)propionic acid [β-(p-methoxycarbonylaminophenyl)lactic acid]

Suitable salts of the compound (I) are conventional non-toxic salt and may include a salt with a base or an acid addition salt such as a salt with an inorganic base, for example, an alkaline metal salt [e.g. sodium salt, potassium salt, cesium salt, etc.], an alkaline earth metal salt [e.g. calcium salt, magnesium salt, etc.], an ammonium salt; a salt with an organic base, for example, an organic amine salt [e.g. triethylamine salt, pyridinium salt, picoline salt, ethanolamine salt, triethanolamine salt, dicyclohexylamine salt, N,N'-dibenzylethylenediamine salt, etc.]; an inorganic acid addition salt [e.g. hydrochloride, hydrobromide, sulfate, phosphate,etc.]; an organic carboxylic or sulfonic acid addition salt [e.g. formate, acetate, trifluoroacetate, maleate, tartrate, methanesulfonate, benzenesulfonate, p-toluenesulfonate, etc.]; a salt with a basic or acidic amino acid [e.g. arginine salt, aspartic acid salt, glutamic acid salt, etc.]; and the like.

In the above and subsequent descriptions of the present specification, suitable examples and illustrations of the various definitions to be included within the scope of the invention are explained in detail as follows.

The term "lower" is intended to mean 1 to 6 carbon atom (s), preferably 1 to 4 carbon atom (s), unless otherwise indicated.

Suitable substituent (s) in the term "benzyl group which has substituent (s)" may include hydroxy, lower alkoxy, lower-alkoxy-lower-alkoxy, lower-alkoxy-lower-alkoxy-lower-alkoxy, lower alkyl, amino, protected amino, mono- or di- substituted lower alkyl amino, cyclic amino, nitro, halogen [e.g. fluoro, chloro, bromo, iodo, etc.], and the like. These may have one or more than one substituents.

Suitable "lower alkyl" may include a straight or branched one having 1 to 6 carbon atom (s) such as methyl, ethyl, n-propyl, isopropyl, butyl, isobutyl, t-butyl, pentyl, hexyl.

Suitable "lower alkoxy" may include methoxy, ethoxy, propoxy, isopropoxy, butoxy, isobutoxy, pentyloxy, isopentyloxy, hexyloxy, and the like.

Suitable "lower-alkoxy-lower-alkoxy" may include methoxymethoxy, methoxyethoxy, methoxypropoxy, ethoxyisopropoxy, and the like.

Suitable "lower-alkoxy-lower-alkoxy-lower-alkoxy" may include methoxymethoxyethoxy, methoxyethoxyethoxy, methoxyethoxypropoxy, ethoxymethoxyisopropoxy, and the like.

Suitable "cyclic amino" may be an aromatic ring or an alicycliccompound which has one or more than one nitrogen atom (s) as hetero atom (s) and may be monocyclic or condensed polycyclic group which may be saturated or unsaturated. Cyclic amino group may further contain hetero atom (s) such as one or more than one nitrogen atom (s), oxygen atom (s), sulfur atom (s), and the like.

Still further the cyclicamino group may be a spiro ring or a bridged cyclic compound. The number of the constructive atoms of the cyclic amino group is not limited but, for example, monocyclic group has a 3 to 8-membered ring and bicyclic group has 7 to 11-membered rings.

Example of such cyclic amino may include saturated or unsaturated monocyclic group containing one nitrogen atom as hetero atom such as 1-azetidinyl, pyrrolidino, 2-pyrroline-1-yl, 1-pyrrolyl, piperidino, 1,4-dihydropyridine-1-yl, 1,2,5,6-tetrahydropyridine-1-yl, homopiperidino; saturated or unsaturated monocyclic group containing more than one nitrogen atoms as hetero atoms such as 1-imidazolidinyl, 1-imidazolyl, 1-pyrazolyl, 1-triazolyl, 1-tetrazolyl, 1-piperazinyl, 1-homopiperazinyl, 1,2-dihydropyridazine-1-yl, 1,2-dihydropyrimidine-1-yl, perhydropyrimidine-1-yl, 1,4-diazacycloheptane-1-yl; saturated or unsaturated monocyclic group containing 1 to 2 oxygen atom (s) and 1 to 3 nitrogen atom (s) as hereto atoms such as oxazolidine-3-yl, 2,3-dihydroisoxazole-2-yl, morpholino; saturated or unsaturated monocyclic group containing 1 to 2 sulfur atom (s) and 1 to 3 nitrogen atom (s) as hetero atoms such as thiazolidine-3-yl, isothiazoline-2-yl, thiomorpholino; condensed polycyclic group such as indole-1-yl, 1,2-dihydrobenzimidazole-1-yl, perhydropyrrolo[1,2-a]pyrazine-2-yl; spirocyclic group such as 2-azaspiro[4,5]decane-2-yl; bridged heterocyclic group such as 7-azabicyclo[2,2,1]heptane-7-yl; and the like.

Suitable "mono- or di-lower alkylamino" may include amino group substituted by one or two lower alkyl (s) [e.g. methyl, ethyl, isopropyl, t-butyl, t-pentyl, etc.], preferably methylamino, ethylamino, dimethylamino, diethylamino, di-n-propylamino, diisopropylamino, dibutylamino, etc.

"Amino protective group" and "Amino protective group" in the term "protected amino" may include acyl such as lower alkanoyl [e.g. formyl, acetyl, propionyl, pivaloyl, hexanoyl, etc.], mono (or di or tri) halo (lower) alkanoyl [e.g. chloroacetyl, bromoacetyl, dichloroacetyl, trifluoroacetyl, etc.], lower alkoxycarbonyl [e.g. methoxycarbonyl, ethoxycarbonyl, propoxycarbonyl, t-butoxycarbonyl, t-pentyloxycarbonyl, hexyloxycarbonyl, etc.], carbamoyl, aroyl [e.g. benzoyl, toluoyl, naphthoyl, etc.], ar (lower) alkanoyl [e.g. phenylacetyl, phenylpropionyl, etc.], aryloxycarbonyl [e.g. phenoxycarbonyl, naphthyloxycarbonyl,etc.], aryloxy (lower) alkanoyl [e.g. phenoxyacetyl, phenoxypropionyl, etc.], arylglyoxyloyl [e.g. phenylglyoxyloyl, naphthylglyoxyloyl, etc.], ar (lower) alkoxycarbonyl which may have suitable substituent (s) [e.g. benzyloxycarbonyl, phenethyloxycarbonyl, p-nitrobenzyloxycarbonyl, etc.]; ar (lower)alkyl such as ar (lower)alkylidene which may have substituent (s) [e.g. benzylidene, hydroxybenzylidene, etc.], mono (or di or tri) phenyl (lower) alkyl [e.g. benzyl, phenethyl, benzhydryl, trityl, etc.]; and the like.

Above-mentioned amino protective group contains the protective group which has the function to temporarily protect amino group and is often used in the field of amino acid and peptide chemistry.

Suitable "benzyl group which has lower alkoxy" may include lower alkoxy-substituted-benzyl such as 4-methoxybenzyl, 2,4-dimethoxybenzyl, 3,4-dimethoxybenzyl, 3,4,5-trimethoxybenzyl, 2,3,4-trimethoxybenzyl, 2-ethoxybenzyl, 4-hexyloxybenzyl, etc.

Suitable "benzyl group which has halogen" may include halogen substituted-benzyl such as 2-fluorobenzyl, 3-fluorobenzyl, 4-fluorobenzyl, 2-chlorobenzyl, 4-chlorobenzyl, 2,4-dichlorobenzyl, 3,4-dichlorobenzyl, 2,6-dichlorobenzyl, 2-bromobenzyl, 2-bromo-4-chlorobenzyl, etc.

Suitable "benzyl group which has lower alkyl" may include lower alkyl-substituted-benzyl such as 4-methylbenzyl, 4-ethylbenzyl, 4-propylbenzyl, 4-isopropylbenzyl, 4-butylbenzyl, 4-isobutylbenzyl, 4-t-butylbenzyl, 4-pentylbenzyl, 4-hexylbenzyl, 2,3-dimethylbenzyl, 2,6-dimethylbenzyl, 3,4-dimethylbenzyl, 2,4,6-trimethylbenzyl,etc.

Suitable example of benzyl group which has such substituent (s) may include lower alkoxy-substituted benzyl [e.g. 4-methoxybenzyl, 3,4-dimethoxybenzyl, 3,4,5-trimethoxybenzyl, 2,3,4-trimethoxybenzyl, 2-ethoxybenzyl, 4-hexyloxybenzyl, etc.], halogen substituted benzyl [e.g. 2-chlorobenzyl, 4-chlorobenzyl, 2,4-dichlorobenzyl, 3,4-dichlorobenzyl, 2,6-dichlorobenzyl, 2-bromobenzyl, 2-bromo-4-chlorobenzyl, etc.], hydroxy-substituted-benzyl [e.g. 2-hydroxybenzyl, 3-hydroxybenzyl, 4-hydroxybenzyl, etc.], and the like.

More preferable example of "cyclic amino group which may have substituent (s)" may include 4-methylpiperazino, and the like.

The processes for preparing the object compound (I) are explained in detail in the following.

Process 1

The object compound (I) or salts thereof can be prepared by subjecting the compound (II) or its reactive derivative at the amino group or carboxy group or a salt thereof to cyclization reaction.

The starting compound (II), its reactive derivative or a salt thereof are new and can be prepared by the methods of Preparations mentioned below or a similar manner thereto.

Suitable reactive derivative at the amino group of the compound (II) may include Schiff's base type imino or its tautomeric enamine type isomer formed by the reaction of the compound (II) with a carbonyl compound such as aldehyde and ketone; a silyl derivative formed by the reaction of the compound (II) with a silyl compound such as bis (trimethylsilyl) acetamide, mono (trimethylsilyl) acetamide, bis (trimethylsilyl) urea; a derivative formed by the reaction of the compound (II) with phosphorus trichloride or phosgene, and the like.

Suitable reactive derivative at the carboxy group of the compound (II) may include an acid halide,an acid anhydride, an activated amide, an activated ester, and the like. Suitable example of the reactive derivative may be an add chloride; an acid azide; a mixed acid anhydride with an acid such as aliphatic carboxylic add [e.g. acetic acid, propionic acid, butyric acid, trichloroacetic acid, etc.] or aromatic carboxylic acid [e.g. benzoic acid, etc.]; a symmetrical acid anhydride, and the like. These reactive derivatives can optionally be selected from them according to the kind of the compound (II) to be used.

The reaction is carried out in the usual method which is used in cyclization reaction, for example, under heating or in the presence of a conventional condensing agent. When R in the compound (II) is amino protective group, the elimination of the amino protective group is carried out prior to ring cyclization reaction.

Suitable condensing agent may include carbodiimide or a salt thereof [e.g. N,N'-dicyclohexylcarbodiimide, N-cyclohexyl-N'-morpholinoethylcarbodiimide, N-cyclohexyl-N'-(4-diethylaminocyclohexyl) carbodiimide, N-ethyl-N'-(3-dimethylaminopropyl) carbodiimide or hydrochloride thereof], diphenyl phosphorylazide, diethyl phosphorocyanidate, bis (2-oxo-3-oxazolidinyl) phosphinic chloride, etc.; N,N'-carbonyldiimidazole, N,N'-carbonylbis-(2-methylimidazole); keteneimine compounds [e.g. pentamethyleneketene-N-cyclohexylimine, diphenylketene-N-cyclohexylimine, etc.]; ethoxyacetylene; 1-alkoxy-1-chloroethylene; ethyl polyphosphate; isopropyl polyphosphate; phosphorus oxychloride (phosphoryl chloride); phosphorus trichloride; thionyl, chloride; oxalyl chloride; combination of triphenylphosphine and carbon tetrachloride or diazene carboxylate; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H -benzotriazole; 1-hydroxybenzotriazole; so-called Vilsmeierreagent prepared b), the reaction of N,N-dimethylformamide with thionyl chloride, phosgene, phosphorus oxychloride,etc.; or the like.

The reaction in the presence of a condensing agent is usually carried out in a conventional organic solvent which does not adversely influence the reaction such as methylene chloride, methanol, ethanol, propanol, acetonitrile, pyridine, N,N-dimethylformamide, 4-methyl-2-pentanone, tetrahydrofuran, benzene, toluene, xylene, etc. or a mixture thereof.

The reaction temperature is not critical and the reaction is usually carried out under cooling to heating. Further, cyclization reaction under heating can be carried out in the above-mentioned organic solvent under heating below boiling point of the solvent.

Process 2

The object compound (Ia) or salts thereof can be prepared by subjecting the compound (III) or a salt thereof to nitration reaction.

The starting compounds (III) contain known compounds (Japanese Kokai Tokkyo Koho 5-170749) and novel compounds. The novel compounds can be prepared by the methods of Preparations and Examples mentioned below or a similar manner thereto.

This reaction is carried out by reacting the compound (III) or a salt thereof with a nitration agent [e.g. nitric acid, nitrate, nitric acid ester, acetyl nitrate, nitronium tetrafluoroborate, etc.].

The reaction can usually be carried out in a conventional solvent which does not adversely influence the reaction such as methylene chloride.

The reaction temperature is not critical and the reaction is usually carried out under cooling or at ambient temperature.

This reaction can be carried out in substantially the same manner as Example 4 mentioned below.

Process 3

The object compound (Ib) or salts thereof can be prepared by subjecting the compound (Ia) or a salt thereof to reduction reaction.

This reaction can be carried out in a conventional manner for reducing nitro to amino and it may include chemical reduction and catalytic reduction.

Suitable reducing agents to be used in chemical reduction are a combination of a metal [e.g. tin, zinc, iron, etc.] or a metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.], and the like.

The reduction is usually carried out in a conventional solvent which does not adversely influence the reaction such as water, methanol, ethanol, propanol, N,N-dimethylformamide or a mixture thereof. Additionally, in case that the above-mentioned acids to be used in chemical reduction are liquid, they can also be used as a solvent. Further, a suitable solvent to be used in catalytic reduction may be the above-mentioned solvent and other conventional solvent such as diethyl ether, dioxane, tetrahydrofuran, or a mixture thereof.

The reaction temperature of this reaction is not critical and the reaction is usually carried out under cooling to warming.

Process 4

The object compound (Ic) or salts thereof can be prepared by subjecting compound (Ib) or a salt thereof, obtained by the Process 3 with or without isolation thereof, to alkylation reaction. This reaction can be carried out by combination of aldehyde and reducing agent, or alkyl halide and base.

Suitable reducing agents may include metal hydride complex compound [e.g. sodium borohydride, sodium cyanoborohydride, potassium borohydride, bis (2-methoxyethoxy) aluminium hydride, etc.], hydrogen, formic acid or ammonium formate, palladium catalyst [e.g. palladium on carbon, palladium hydroxide on carbon, palladium black,etc.].

Suitable base may include an inorganic base [e.g. sodium bicarbonate, potassium carbonate, etc.] and an organic base [e.g. pyridine, triethylamine, etc.].

The reaction is usually carried out in a conventional solvent which does not adversely influence the reaction.

The reaction by combining aldehyde and reducing agent can be carried out in substantially the same manner as Preparation 2 mentioned below.

The reaction by combining alkyl halide and base can be carried out in substantially the same manner as Preparation 13 mentioned below.

Process 5

The object compound (Id) or salts thereof can be prepared by subjecting compound (Ib) or a salt thereof, obtained by the Process 3 with or without isolation thereof, to monoalkylation reaction followed by intramolecular alkylation reaction. This reaction can be carried out by combining a compound having two aldehydes in the molecule and a reducing agent, or by combining a compound having two halogens in the molecule and a base.

Process 6

The object compound (Ie) or salts thereof can be prepared by subjecting compound (Ib) or a salt thereof, obtained by the Process 3 with or without isolation thereof, to hydroxylation reaction by diazotization reaction followed by decomposition of diazonium salt. This reaction can be carried out by reacting the compound (Ib) or a salt thereof with sodium nitrite in the presence of an inorganic or an organic acid and decomposing a growing diazonium salt in water or an organic acid under the room temperature to heating, carrying out hydrolysis if necessary. It is possible to prepare the compound (Ie) or salts thereof by transforming the amino group of the compound (Ib) or a salt thereof into a hydroxyl group.

Suitable acid may include an inorganic acid [e.g. sulfuric acid, hydrochloric acid, borofluoric acid, etc.] and an organic acid [e.g. acetic acid, trifluoroacetic acid, etc.].

Process 7

The object compound (If) or salts thereof can be prepared by subjecting the compound (Ie) or a salt thereof, which is obtained by the Process 6, to alkylation reaction. This reaction can be carried out by combining a alkyl halide and a base.

Suitable base may include an inorganic base [e.g. sodium bicarbonate, potassium carbonate, etc.] and an organic base [e.g. pyridine, triethylamine, etc.].

Process 8

The object compound (Ih) or salts thereof can be prepared by subjecting the compound (Ig) or a salt thereof to removal reaction of the amino protective group.

This removal reaction is carried out in a conventional manner such as hydrolysis,reduction or the like.

The hydrolysis is preferably carried out in the presence of a base or an acid including Lewis acid.

Suitable base may include an inorganic base and an organic base such as an alkaline metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo [4.3.0]non-5-ene, 1,4-diazabicyclo [2.2.2] octane, 1,8-diazabicyclo [5.4.0]undec-7-ene, or the like.

Suitable acid may include an organic acid [e.g. formic acid, acetic acid, propionic acid, trichloroacetic acid, trifluoroacetic acid, p-toluenesulfonic acid, etc.] and an inorganic acid [e.g. hydrochloric acid, hydrobromic acid, sulfuric acid, hydrogen chloride, hydrogen bromide, ammonium chloride, etc.]. The removal reaction using Lewis acid such as trihaloacetic acid [e.g. trichloroacetic acid, trifluoroacetic acid, etc.] is preferably carried out in the presence of cation trapping agents [e.g. anisole,phenol, etc.].

The reaction is usually carried out in a solvent such as water, alcohol [e.g. methanol, ethanol, etc.], tetrahydrofuran, methylene chloride, a mixture thereof or any other solvent which does not adversely influence the reaction. A liquid base or acid can be also used as a solvent.

The reaction temperature is not critical and the reaction is usually carried out under cooling to warming.

The reduction which can be used for removal reaction includes chemical reduction and catalytic reduction.

Suitable reducing agents to be used in chemical reduction are a combination of a metal [e.g. tin, zinc, iron, etc.] or a metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction may include platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide or a mixture thereof. Additionally, in case that the above-mentioned acids to be used in chemical reduction are liquid, they can also be used as a solvent.

The reaction temperature of this reaction is not critical and the reaction is usually carried out under cooling to warming.

The compound or its salt of the present invention has excellent parasiticidal activities as parasiticides (anthelmintics) for animals and human bodies. Particularly it is effective against nematodes, trematodes and cestodes which are infective to the domestic animals, domestic fowls or pets such as pigs, sheep, goats,cattle, horses, dogs, cats and chickens.

Nematodes which can be effectively exterminated by the compound are shown in the following:

Haemonchus genus, Trichostrongylus genus, Ostertagia genus, Nematodirus genus, Cooperia genus, Ascaris genus, Bunostomum genus, Oesophagostomum genus, Chabertia genus, Trichuris genus, Strongylus genus, Trichonema genus, Dictyocaulus genus, Capillaria genus, Heterakis genus, Toxocara genus, Ascaridia genus, Oxyuris genus, Ancylostoma genus, Uncinaria genus, Toxascaris genus, Parescaris genus, Nippostrongylus genus, Metastrongylus genus, Hyostrongylus genus, Strongyloides genus and Cyathostomum genus.

Some kinds of Nematodirus genus, Cooperia genus and Oesophagostomum genus attack the intestinal canal, just Haemonchus genus and Ostertagia genus are parasitic on the stomach and parasites of Dictyocaulus genus are found in lungs. The compound is effective against them.

The parasites of Filariidae or Setariidae are found in other tissues and organs such as heart, blood vessels, hypodermis, lymphatic vessels. The compound is also effective against them.

Trematodes which can be effectively exterminated by the compound are shown in the following:

Fasciola genus, Calicophoron genus, Orthocoelium genus and Eurytrema genus.

Cestodes which can be effectively exterminated by the compound are shown in the following:

Anoplocephala genus, Moniezia genus and Dipylidiumc genus.

It is also effective against parasites which infect human beings. The most common parasites in the alimentary canal of human beings are as follows:

Ancylostoma genus, Necator genus, Ascaris genus, Strongyloidesgenus, Trichinella genus, Capillaria genus, Trichuris genus and Enterobius genus.

It is also effective against other medically important parasites which is found in the blood or other tissues or organs outside of the alimentary canal, such as Wuchereria genus, Brugia genus, Onchocerca genus and Loa genus in Filariidae, as well as parasites such as Dracunlus genus in Dracunculidae. It is also effective against parasites in the intestinal canal such as Strongyloides genus, Trichinellagenus in a particularly conditioned parasitism outside of the intestinal canal.

Specifically, relationships between different animals and nematodes, trematodes and cestodes parasitic on those animals are as follows:

Parasites parasitic on cattle include stomach worms living in the stomach (Haemonchus, Ostertagia, Trichostrongylus, Cooperia), hookworms living in the small intestine (Bunostomum), trichina (Strongyloides), nematodes (Nematodirus), cestodes (Monizia), roundworms living in the large intestine (Oesophagostomum, Trituris), liver flukes living in the liver (Fasciola), and lungworms living in the lungs (Dictyocaulus).

Parasites parasitic on sheep include stomach worms living in the stomach (Haemonchus, Ostertagia, Trichostrongylus), parasites living elsewhere in the gastrointestinal (Bunostomum, Trichostrongylus, Cooperia, Strongyloides, Oesophagostomum, Taenia, Chabertia, Trituris), lungworms living in the lungs (Dictyocaulus, Muellerius, Protostrongylus), and liver flukes living in the liver (Fasciola, Dicrocoelium).

Parasites parasitic on pigs include stomach worms living in the stomach (Hyostrongyloides), roundworms living in the small intestine (Ascaris), trichina (Strongyloides), hog intestine tubercle worms living in the cecum (Oesophagostomum), whipworms (Trituris), lungworms living in the lungs (Metastrongylus), and liver flukes living in the liver (Fasciola).

Parasites parasitic on horses include stomach worms living in the stomach (Habronema, Draschia), roundworms living in the small intestine (Parascaris), trichina (Strongyloides), cestodes (Anoplocephala), pinworms living in the large intestine (Oxyuris), liver flukes living in the liver (Fasciola), and lungworms living in the lungs (Dictyocaulus).

Parasites parasitic on dogs include roundworms living in the small intestine (Toxocara, Toxascaris), hookworms (Ancylostoma, Uncinaria), trichina (Strongyloides), cestodes (Dipylidium, Taenia), lungworms living in the lungs (Capillaria), and filariid worms living in the heart (Dirofilaria).

The compound of this invention also kills plant nematodes and soil nematodes, and therefore can be used as a pest controller in agriculture, grape growing, fruit growing, landscape gardening and afforestation.

In order to illustrate the usefulness of the object compound (I), the pharmacological test data of the representative compounds of the compound (I) are shown in the following.

Test

Test 1

(1) Test Compound The compound of Example 1.

(2) Test Method

The effect of parasiticides (anthelmintics) was examined with the rats which was infected by nematodes which are parasitic on rats, Nippostrongylus brasilienses.

Wistar strain rats (female, 6 weeks old, 120–130 g weight) were sacrificed by infecting them and giving them subcutaneous injections of 3000 infective larvae per rat.

Test compound of 50 mg was dissolved in 0.25 ml dimethylsulfoxide, 0.5% methylcellulose aqueous solution was added, and liquid volume was adjusted to be prescribed volume of 100, 20, 10, 5, 2.5, 1.25, 1.0, 0.63, 0.32 mg/kg to utilize. After they were infected, on each 7th, 8th and 9th day, the test compound was administered orally with above concentrations. On the 11th day, the rats were dissected and the number of parasites in the small intestine were measured.

The given measurement was based to calculate the reduction rate from the percentage of the number of the parasites of unadministered rats (control).

The result is shown in the Table 1.

(3) Test Result

| Test Compounds | Minimum Amount of Administration indicated by more than 85% of Reduction Rate |
|---|---|
| PF1022 (Japanese Kokai Tokkyo Koho 3 - 35,796) | 10 mg/kg |
| PF1022 - D (Japanese Kokai Tokkyo Koho 5 - 170,749) | 20 mg/kg |
| Example 1 | 5 mg/kg |

Test 2

(1) Test Compound

The compounds of Example 1 and Example 3.

(2) Test Method

Effectivity against microfilaria was examined with the dogs which was confirmed to be infected by heart worm (Dirofilaria immitis).

The capsulated test compounds were orally administered once by compulsion to the infected dogs with the dosage of 100 mg/kg.

Blood was gathered in 18 hours before administration, in 1 hour and on the 1st, 2nd and 7th day after the administration and numbers of microfilaria in the blood were inspected by acetone concentration technique of microfilaria.

The result is shown in the Table 2.

(3) Test Result

TABLE 2

| Test Compounds | Dose (mg/kg) | Before administration 18 hrs. | After administration 1 hrs. | 1 day | 2 day | 7 day |
|---|---|---|---|---|---|---|
| PF1022 - D | 100 | 152,967 | 129,900 | 76,033 | 146,667 | 193,350 |
| Example 1 | 100 | 109,217 | 56,583 | 17 | 33 | 180 |
| Example 3 | 100 | 12,300 | 8,133 | 6,917 | 8,000 | 17 |

Test 3

(1) Test Compound

The compounds which are illustrated in Example 1, Example 2 and Example 3.

(2) Test Method

The growth inhibiting effect on a free-living nematode (Rhabditis elongtus) was studied.

The test compounds were dissolved in methanol and test compound solutions of 2000, 1000, 500, 250, 125 and 62.5 µg/ml were prepared. 1 ml of each of these solutions was dripped onto pre-prepared agar in a petri dish (1.5% agar, 10 ml per petri dish) and well dried. 0.5 ml of a suspension of free-living nematodes (about 100 nematodes/ml) was dripped onto each petri dish, and water of the suspension was evaporated by blow-drying. Yeast powder, which is a nutrient source for nematodes, was sprinkled on the agar, and then the petri dishes were covered in parafilm and left to stand at 25° C. for 24 hours. The effect was judged by observing the worms under a microscope and measuring the minimum concentration of test compound with which eliminated motility, The result is shown in the Table 3.

(3) Test Result

TABLE 3

| Test Compounds | Minimum effective concentration (μg/ml) |
| --- | --- |
| PF1022 - D | >2000 |
| Example 1 | 500 |
| Example 2 | 1000 |
| Example 3 | 1000 |

When the compounds of the present invention are used for animals and human being as parasiticides (anthelmintics), it can be administered orally as a liquid drink. The liquid drink is usually solution, suspension or dispersed solution in a suitable non-toxic solvent or water in admixture with suspending agent such as bentonite, wetting agent or excipient, and it generally contains liquid drink or antifoaming agent. The prescription of a liquid drink generally contains 0.01~0.5 weight%, preferably 0.01~0.1 weight% activated compound. When it is preferably administered orally as a dried solid single dose, capsules, pills, or tablets, which contains the desired amount of activated compound are usually used. These forms of dosage are prepared by homogeneous admixtures of diluent, filler, disintegrator and/or excipient such as dextrine, lactose, talc, magnesium stearate, vegetable rubber. The usage of such single dose prescription can be varied broadly referring to the weight and containing quantity of parasiticides (anthelmintics) depending upon kind of hosts, kind of parasites and weight of hosts which are to be treated.

When it is administered in animal feed, it is used as to disperse homogeneously, or as top dressing, or in the form of pellet. To achieve preferable antiparasitic effect, the activated compound of 0.0001~2% is usually contained in feed.

The dosage which was dissolved or dispersed in liquid carrier excipients can be administered to animals parenterally by giving them injections in the anterior stomach, muscle, trachea, or under the skin. The activated compound is mixed with suitable vegetable oil such as peanut oil, cottonseed oil for parenteral administration. These prescriptions generally contain the activated compound of 0.05~50 weight%.

It can also be administered locally by mixing in a suitable carrier such as dimethylsulfoxide or hydrocarbon solvent. The prepared pharmaceutical can be used directly on the exterior of animals by spraying or direct injections.

Among the compounds of the invention, compounds which are hardly soluble in water are improved in its absorption characteristics into alimentary canal by various well-known pharmaceutical techniques for improving solubility. The pharmaceutical techniques concerning the matter may include the method for preparing a pharmaceutical composition containing at least one kind of surfactants and/or fats and oils (Japanese Kokai Tokko Koho 4-221312, 5-70366), the method for dispersing a medicine of solid state into an inactive carrier in monomolecular state (Japanese Kokai Tokko Koho 5-262642), and the like.

Concretely the surfactant may include fatty acid esters of glycerine, fatty acid esters of sorbitan, fatty acid esters of polyoxyethylene sorbitan, fatty acid esters of polyoxyethylene glycerine, polyoxyethylene hydrogenated castor oils, fatty acid esters of sucrose, polyoxyethylene polyoxypropylene glycol, polysorbate, and the like. The fat and oil may include soybean oil, tallow, hydrogenated oils, almond oil, olive oil, sesame oil, and the like. The inactive carrier may include low viscosity hydroxypropyl cellulose, and the like.

The most suitable usage amount of the activated compound to achieve the most effective result depends on the kind of animals which are to be treated, and type of parasitic infection and its stage.

It can be achieved by oral administration of the activated compound 0.01~100 mg, preferably 0.5~50.0 mg per kg of the treated animal.

Such dosage amount is given in a relatively short term of 1~5days at once or separately.

The following Preparations and Examples are given for the purpose of illustrating the present invention.

Preparation 1

To a solution of ethyl (R)-2-acetoxy-3-(4-nitrophenyl) propionate (5.62 g) in ethanol (50 ml) was added conc. hydrochloric acid (2.5 ml) and 10% palladium on carbon (0.6 g) and the mixture was hydrogenated under atmospheric pressure of hydrogen gas for 3 hours at ambient temperature. The catalyst was filtered off and the filtrate was evaporated in vacuo. To the obtained residue was added 0.05N Hydrochloric acid (200 ml) and washed with ether (100 ml×2). Saturated sodium bicarbonate aqueous solution was added to aqueous layer until pH10 and extracted with ether (100 ml×4).

Combined ethereal layer was washed with brine and then was dried over anhydrous sodium sulfate and evaporated in vacuo. To the residue, benzene (40 ml), benzyl alcohol (21 ml) and p-toluenesulfonic acid.monohydrate (4.76 g) were added and the mixture was heated under reflux for 4 hours. After cooling down to room temperature, the solvent was evaporated in vacuo. To the residue was added water (200 ml) and washed with ether (100 ml×2). Saturated sodium bicarbonate aqueous solution was added to aqueous layer until pH10 and extracted with ether (100 ml×4). Combined ethereal layer was washed with brine, dried over anhydrous sodium sulfate and evaporated in vacuo to give benzyl (R)-3-(4-aminophenyl)-2-hydroxypropionate (2.84 g).

NMR (CDCl$_3$, δ) 2.85 (dd, 1H), 2.6–3.6 (m, 3H), 3.00 (dd, 1H), 4.38 (dd, 1H), 5.15 (s, 2H), 6.53 (d, 2H), 6.90 (d, 2H), 7.25–7.4 (m, 5H)

IR (neat):1740 cm$^{-1}$

Preparation 2

To a solution of benzyl (R)-3-(4-aminophenyl)-2-hydroxypropionate (0.26 g) in acetic acid (6 ml) was added paraformaldehyde (0.3 g), and further sodium cyanoborohydride (0.3 g) was added gradually, and stirred for 3 hours at ambient temperature. To sodium bicarbonate solution (25 ml) and ice (25 g) was added reaction mixture gradually and was extracted with ethyl acetate (50 ml×2). The separated ethyl acetate layer was washed with brine,dried over anhydrous sodium sulfate and evaporated in vacuo. The resultant crude product was subjected to column chromatography on silica gel eluting with a mixture of hexane and ethyl acetate (7:3 by volume). The fractions containing the desired product were combined and evaporated in vacuo to give benzyl (R)-3-(4-dimethylaminophenyl)-2-hydroxypropionate (0.22 g).

NMR (CDCl$_3$, δ) 2.64 (d, 1H), 2.91 (s, 6H), 2.90 (dd, 1H), 3.04 (dd, 1H), 4.43 (ddd, 1H), 5.18 (s, 2H), 6.63 (d, 2H), 7.01 (d, 2H), 7.35 (bs, 5H)

IR (neat):1.733, 1612 cm$^{-1}$

Preparation 3

To a solution of Boc-MeLeu-OH (1.27 g) and H-D-p-Me$_2$NPhLac-OBzl (1.47 g) in methylene chloride (20 ml) were added dimethylaminopyridine (0.15 g) and 1-ethyl-3-(3-dimethylaminopropyl) carbodiimide.hydrochloride (1.01 g) under ice-cooling and stirred for 15 hours. The solvent was evaporated in vacuo and then water (50 ml) was added to the residue and extracted with ethyl acetate (50 ml×3). The ethyl acetate layer was washed with brine, dried over anhydrous sodium sulfate and evaporated in vacuo. The resultant crude product was subjected to column chromatography on silica gel eluting with a mixture of hexane and ethyl acetate (4:1 by volume). The fractions containing the desired product were combined and evaporated in vacuo to give Boc-MeLeu-D-p-Me$_2$NPhLac-OBzl (1.69 g).

NMR (CDCl$_3$, δ) 0.90 (d, 6H), 1.4–1.65 (m, 12H), 2.63 (s) and 2.68 (s) (3H), 2.93 (s, 6H), 3.05–3.15 (m, 2H), 4.65–4.80 (m) and 4.95–5.20 (m) (4H), 6.62 (d, 2H), 7.03 (d, 2H), 7.1–7.2 (m, 5H)

IR (KBr):1747, 1730, 1693, 1675, cm$^{-1}$

Preparation 4

To a solution of Boc-MeLeu-D-p-Me$_2$NPhLac-OBzl (1.67 g) in a mixed solvent of methanol (30 ml) and tetrahydrofuran (5 ml) was added 10% palladium-charcoal (0.3 g) and the mixture was subjected to hydrogenation reaction under hydrogen atmosphere (1 atm.) at ambient temperature for 1.5 hours. The catalyst was filtered off and the filtrate was evaporated in vacuo to give Boc-MeLeu-D-p-Me$_2$NPhLac-OH (1.44 g).

IR (KBr):1741,1694 cm$^{-1}$

Preparation 5

Boc-MeLeu-D-Lac-OBzl (2.45 g) was used instead of Boc-MeLeu-D-p-Me$_2$NPhlac-OBzl. Except above matter, Boc-MeLeu-D-Lac-OH (1.77 g) was obtained according to a similar manner to that of Preparation 4.

IR (KBr):1.742, 1695, 1668 cm$^{-1}$

Preparation 6

To a mixture of Boc-MeLeu-D-Lac-OH (1.76 g), H-MeLeu-D-Lac-OBzl (2.05 g), methylene chloride (40 ml) and triethylamine (1.7 ml) was added bis (2-oxo-3-oxazolidinyl) phosphinic chloride (1.55 g) under ice-cooling and stirred for 28 hours. Water (100 ml) was added to the reaction mixture and extracted with ethyl acetate (50 ml×3). The ethyl acetate layer was washed with brine, dried over anhydrous sodium sulfate and evaporated in vacuo. The resultant crude product was subjected to column chromatography on silica gel eluting with a mixture of ethyl acetate and hexane (3:7 by volume). The fractions containing the desired product were combined and evaporated in vacuo to give Boc-MeLeu-D-Lac-MeLeu-D-Lac-OBzl (2.29 g).

NMR(CDCl$_3$, δ):0.85–1.00 (m, 12H), 1.35–1.90 (m, 12H), 1.45 (s, 9H),2.80–2.95 (m, 6H), 4.45–5.40 (m, 6H), 7.35 (bs, 5H)

IR(neat):1741, 1693,1667 cm$^{-1}$

Preparation 7

Boc-MeLeu-D-Lac-MeLeu-D-Lac-OBzl (0.775 g) was used instead of Boc-MeLeu-D-p-Me$_2$NPhLac-OBzl. Except above matter, Boc-MeLeu-D-Lac-MeLeu-D-Lac-OH (0.62 g) was obtained according to a similar manner to that of Preparation 4.

IR (neat):1740, 1695, 1666 cm$^{-1}$

Preparation 8

Boc-MeLeu-D-Lac-MeLeu-D-Lac-OH (3.51 g) was used instead of Boc-MeLeu-D-Lac-OH. Except above matter, Boc-MeLeu-D-Lac-MeLeu-D-Lac-MeLeu-D-Lac-OBzl (4.89 g) was obtained according to a similar manner to that of Preparation 6.

NMR (CDCl$_3$, δ) 0.80–1.05 (m, 18H), 1.2–1.85 (m, 27H), 2.8–3.1 (m, 9H), 4.70–4.8 (m) and 4.9–5.5 (m) (6H), 7.3–7.4 (m, 5H)

IR (KBr):1741, 1695, 1665 cm$^{-1}$

Preparation 9

Boc-MeLeu-D-Lac-MeLeu-D-Lac-MeLeu-D-Lac-OBzl (4.89 g) was dissolved in 4N-hydrogen chloride in ethyl acetate (30 ml) and stirred for 2 hours at ambient temperature. After the solvent was evaporated in vacuo, the residue was azeotroped twice by toluene (20 ml). Hexane (10 ml) and methylene chloride (10 ml) were added and the solvents were evaporated in vacuo. This procedure was repeated twice to give HCl.H-MeLeu-D-Lac-MeLeu-D-Lac-MeLeu-D-Lac-OBzl (4.97 g).

IR (KBr):1742, 1647 cm$^{-1}$

Preparation 10

To a mixture of Boc-MeLeu-D-p-Me$_2$NPhLac-OH (0.82 g), HCl. H-MeLeu-D-Lac-MeLeu-D-Lac-MeLeu-D-Lac-OBzl (1.27 g), N-methylmorpholine (0.85 ml) and methylene chloride (10 ml) was added bis (2-oxo-3-oxazolidinyl) phosphinic chloride (0.72 g) under ice-cooling and stirred for 15 hours. The reaction mixture was evaporated in vacuo, water (50 ml) was added and extracted with ethyl acetate (50 ml×3). The ethyl acetate layer was washed with brine, dried over anhydrous sodium sulfate and evaporated in vacuo. The resultant crude product was subjected to column chromatography on silica gel eluting with a mixture of hexane, ethyl acetate and ethanol (1:3:0.1 by volume). The fractions containing the desired product were combined and evaporated in vacuo to give Boc-MeLeu-D-p-Me$_2$NPhLac-MeLeu-D-Lac-MeLeu-D-Lac-MeLeu-D-Lac-OBzl (0.69 g).

IR (KBr):1740, 1695, 1663 cm$^{-1}$ $^{FAB-MS:}$1024[M-Boc+H]$^+$

Preparation 11

Boc-MeLeu-D-p-Me$_2$NPhLac-MeLeu-D-Lac-MeLeu-D-Lac-MeLeu-D-Lac-OBzl (0.69 g) was used instead of Boc-MeLeu-D-p-Me$_2$NPhLac-OBzl. Except above matter, Boc-MeLeu-D-p-Me$_2$NPhLac-MeLeu-D-Lac-MeLeu-D-Lac-MeLeu-D-Lac-OH (0.67 g) was obtained according to a similar manner to that of Preparation 4.

IR (KBr):1739, 1694, 1663 cm$^{-1}$

Preparation 12

Boc-MeLeu-D-p-Me$_2$NPhLac-MeLeu-D-Lac-MeLeu-D-Lac-MeLeu-D-Lac-OH (0.67 g) was used instead of Boc-MeLeu-D-Lac-MeLeu-D-Lac-MeLeu-D-Lac-OBzl. Except above matter, 2HCl. H-MeLeu-D-p-Me$_2$NPhLac-MeLeu-D-Lac-MeLeu-D-Lac-MeLeu-D-Lac-OH (0.60 g) was obtained according to a similar manner to that of Preparation 9.

IR (KBr):1741, 1640 cm$^{-1}$

Preparation 13

A suspended solution of benzyl (R)-3-(4-aminophenyl)-2-hydroxypropionate (0.27 g), bis (2-chloroethyl) ether (0.12 ml), potassium carbonate (0.28 g) and sodium iodide (0.075 g) in dimethylformamide (1 ml) was heated at 70°–90° C. for 7 hours. After cooling down to room temperature, water (50 ml) was added and extracted with ether (25 ml×3). The ether layer was washed with brine, dried over anhydrous sodium sulfate and evaporated in vacuo. The resultant crude product was subjected to column chromatography on silica gel eluting with a mixture of hexane, ethyl acetate and ethanol (60:35:5 by volume). The fractions containing the desired product were combined and evaporated in vacuo to give benzyl (R)-2-hydroxy-3-(4-morpholinophenyl) propionate (0.14 g).

NMR (CDCl$_3$, δ) 2.66 (d, 1H), 2.91 (dd, 1H), 3.05 (dd, 1H), 3.0–3.15 (m, 4H), 3.8–3.95 (m, 4H), 4.45 (ddd, 1H), 5.18 (s, 2H), 6.79 (d, 2H), 7.05 (d, 2H), 7.3–7.4 (m, 5H)

IR (neat):1734 cm$^{-1}$ $^{EI-MS}$ 341[M]$^+$

Preparation 14

H-D-p-MorPhLac-OBzl (0.90 g) was used instead of H-D-p-Me$_2$NPhLac -OBzl. Except above matter, Boc-MeLeu-D-p-MorPhLac-OBzl (1.36 g) was obtained according to a similar manner to that of Preparation 3.

NMR (CDCl$_3$, δ) 0.9 (d, 6H) 1.4–1.65 (m, 12H), 2.63 (s) and 2.66 (s) (3H), 3.05–3.2 (m, 6H), 3.85–3.95 (m, 4H), 4.7–4.8 (m) and 4.95–5.25 (m) (4H), 6.80 (d, 2H), 7.07 (d, 2H), 7.1–7.2 (m, 5H)

IR (KBr):1740, 1695 cm$^{-1}$

Preparation 15

Boc-MeLeu-D-p-MorPhLac-OBzl (1.35 g) was used instead of Boc-MeLeu-D-p-Me$_2$NPhLac-OBzl. Except above matter, Boc-MeLeu-D-p-MorPhLac-OH (1.08 g) was obtained according to a similar manner to that of Preparation 4.

IR (KBr):1742, 1695 cm$^{-1}$

Preparation 16

Boc-MeLeu-D-p-MorPhLac-OH (1.54 g) was used instead of Boc-MeLeu-D-p-Me$_2$NPhLac-OH. Except above matter, Boc-MeLeu-D-p-MorPhLac-MeLeu-D-Lac-MeLeu-D-Lac-MeLeu-D-Lac-OBzl (1.60 g) was obtained according to a similar manner to that of Preparation 10.

NMR (CDCl$_3$, δ) 0.8–1.0 (m, 24H), 1.2–1.9 (m, 30H), 2.7–3.15 (m, 18H), 3.8–3.9 (m, 4H), 4.65–4.75 (m) and 4.9–5.5 (m) (10H), 6.82 (d, 2H), 7.13 (d, 2H), 7.3–7.4 (m, 5H)

IR (KBr):1740, 1695, 1667 cm$^{-1}$ $^{FAB-MS}$:1166[M+H]$^+$

Preparation 17

Boc-MeLeu-D-p-MorPhLac-MeLeu-D-Lac-MeLeu-D-Lac-MeLeu-D-Lac-OBzl (1.59 g) was used instead of Boc-MeLeu-D-p-Me$_2$NPhLac-OBzl. Except above matter, Boc-MeLeu-D-p-MorPhLac-MeLeu-D-Lac-MeLeu-D-Lac-MeLeu-D-Lac-OH (1.56 g) was obtained according to a similar manner to that of Preparation 4.

IR (KBr):1739, 1695, 1680 cm$^{-1}$

Preparation 18

Boc-MeLeu-D-p-MorPhLac-MeLeu-D-Lac-MeLeu-D-Lac-MeLeu-D-Lac-OH (1.56 g) was used instead of Boc-MeLeu-D-Lac-MeLeu-D-Lac-MeLeu-D-Lac-OBzl. Except above matter, 2HCl.H-MeLeu-D-p-MorPhLac-MeLeu-D-Lac-MeLeu-D-Lac-MeLeu-D-Lac-OH 1.66 g) was obtained according to a similar manner to that of Preparation 9.

IR (KBr):1743, 1647 cm$^{-1}$

Preparation 19

Boc-Tyr(Me)-OH (5.1 g) was dissolved in 4N-hydrogen chloride in dioxane (87.5 ml) and stirred for 2 hours under ice-cooling. After dioxane was evaporated in vacuo, the residue was dissolved in 6N-hydrochloric acid aqueous solution (45 ml) and sodium nitrite (1.9 g) was added by portions at 0° C. After stirring for 4 hours, the reaction solution was extracted with ether (100 ml×3). The ether layer was washed with brine, dried over calcium chloride and evaporated in vacuo. To the residue, benzene (30 ml), benzyl alcohol (3.4 ml) and p-toluenesulfonic acid.monohydrate (0.22 g) were added and the mixture was heated under reflux for 3 hours by using Dean Stark apparatus. After cooling down to room temperature, the solvent was evaporated in vacuo. The resultant crude product was subjected to column chromatography on silica gel eluting with a mixture of hexane and ethyl acetate (10:1 by volume). The fractions containing the desired product were combined and evaporated in vacuo to give benzyl (S)-2-chloro-3-(4-methoxyphenyl) propionate (1.79 g). NMR (CDCl$_3$, δ):3.12 (d d, 1 H), 3.29 (d d, 1H), 3.78 (s, 3H), 4.44 (t, 1H), 5.07–5.25 (m, 2H), 6.77–7.36 (m, 9H)

Preparation 20

To a solution of Boc-MeLeu-OH (1.37 g) in a mixed solvent of methanol (30 ml) and water (10 ml) was added 20% cesium carbonate aqueous solution to pH 7.0. After the solvent was evaporated in vacuo, the residue was azeotroped three times by toluene (10 ml). The residue was dissolved in dimethylformamide (20 ml) and then benzyl (S)-2-chloro-3-(4-methoxyphenyl) propionate (1.7 g) was added under ice-cooling and stirred for 24 hours at ambient temperature. The reaction mixture was poured into water (150 ml) and extracted with ether (100 ml×3). The ether layer was washed with brine, dried over anhydrous magnesium sulfate and evaporated in vacuo. The resultant crude product was subjected to column chromatography on silica gel eluting with a mixture of ethyl acetate and hexane (1:8 by volume). The fractions containing the desired product were combined and evaporated in vacuo to give Boc-MeLeu-D-p-MeOPhLac-OBzl (1.59 g).

NMR (CDCl$_3$, δ):0.90 (d, 6H), 1.41 (s) and 1.49 (s) (9H), 1.40–1.58 (m, 3H), 2.62–2.67 (m, 3H), 3.06–3.15 (m, 2H), 3.77 (s, 3H), 4.68–4.80 (m) and, 4.97–5.29 (m) (4H), 6.78 (d, 2H), 7.06 (d, 2H), 7.26–7.36 (m, 5H).

Preparation 21

To a solution of Boc-MeLeu-D-p-MeOPhLac-OBzl (1.36 g) in methanol (15 ml) was added 10% palladium-charcoal (0.4 g) and the mixture was subjected to hydrogenation reaction under hydrogen atmosphere (1 atm.) at ambient temperature for 45 minutes. The catalyst was filtered off and the filtrate was evaporated in vacuo to give Boc-MeLeu-D-p-MeOPhLac-OH (1.08 g).

NMR (CDCl$_3$, δ):0.89–0.95 (m, 6H), 1.44 (s, 9H), 1.44–1.79 (m, 3H), 2.66–2.82 (m, 3H), 3.01–3.20 (m, 2H), 3.79 (s, 3H), 4.40–4.75 (m, 1H), 5.15–5.38 (m, 1H), 6.82 (d, 2H), 7.14 (d, 2H)

Preparation 22

Boc-MeLeu-D-p-MeOPhLac-OH (0.89 g) was used instead of Boc-MeLeu-D-p-Me$_2$NPhLac-OH. Except above matter, Boc-MeLeu-D-p-MeOPhLac-MeLeu-D-Lac-MeLeu-D-Lac-MeLeu-D-Lac-OBzl (1.06 g) was obtained according to a similar manner to that of Preparation 10.

NMR (CDCl$_3$, δ) 0.85–1.0 (m, 24H), 1.4–1.9 (m, 21H), 2.75–3.15 (m, 14H), 3.78 (s, 3H), 4.65–4.75 (m) and 4.9–5.5 (m) (10H), 6.82 (d, 2H), 7.15 (d, 2H), 7.3–7.4 (m, 5H)

IR (KBr):1740, 1695, 1664 cm$^{-1}$ $^{FAB-MS}$:1011[M-Boc+H]$^+$

Preparation 23

Boc-MeLeu-D-p-MeOPhLac-MeLeu-D-Lac-MeLeu-D-Lac-MeLeu-D-Lac-OBzl (1.05 g) was used instead of Boc-MeLeu-D-p-Me$_2$NPhLac-OBzl. Except above matter, Boc-MeLeu-D-p-MeOPhLac-MeLeu-D-Lac-MeLeu-D-Lac-MeLeu-D-Lac-OH (1.06 g) was obtained according to a similar manner to that of Preparation 4.

IR (KBr):1740, 1695, 1664 cm$^{-1}$

Preparation 24

Boc-MeLeu-D-p-MeOPhLac-MeLeu-D-Lac-MeLeu-D-Lac-MeLeu-D-Lac-OH (0.95 g) was used instead of Boc-MeLeu-D-Lac-MeLeu-D-Lac-MeLeu-D-Lac-OBzl. Except above matter, HCl.H-MeLeu-D-p-MeOPhLac-MeLeu-D-Lac-MeLeu-D-Lac-MeLeu-D-Lac-OH (1.01 g) was obtained according to a similar manner to that of Preparation 9.

IR (KBr):1742, 1664 cm$^{-1}$

Preparation 25

To a solution of benzyl (R)-3-(4-aminophenyl)-2-hydroxypropionate (1.36 g) and potassium carbonate (1.04 g) in a mixed solvent of 1,4-dioxane (15 ml) and water (3 ml) was added methyl chlorocarbonate (0.46 ml) dropwise under ice-cooling and stirred for 4 hours. To the reaction mixture water (100 ml) was added and extracted with ethyl acetate (50 ml+25 ml). The ethyl acetate layer was washed with 5% citric acid aqueous solution and brine successively, dried over anhydrous sodium sulfate and evaporated in vacuo. The resultant crude product was subjected to column chromatography on silica gel eluting with a mixture of hexane and ethyl acetate (7:3~6:4 by volume). The fractions containing the desired product were combined and evaporated in vacuo to give benzyl (R)-2-hydroxy-3-(4-methoxycarbonylaminophenyl) propionate (1.65 g).

NMR (CDCl$_3$, δ):1.60 (b s, 1H), 2.93 (dd, 1H), 3.8 (dd, 1H), 3.77 (s, 3H), 4.46 (dd, 1H), 5.18 (s, 2H), 6.58 (bs, 1H), 7.07 (d, 2H), 7.24 (d, 2H), 7.3– 7.4 (m, 5H)

IR (KBr):1714 cm$^{-1}$

Preparation 26

H-D-p-CbmNHPhLac-OBzl (1.35 g) was used instead of H-D-p-Me$_2$NPhLac-OBzl. Except above matter, Boc-MeLeu-D-p-CbmNHPhLac-MeLeu-D-Lac-OBzl (2.82 g) was obtained according to a similar manner to that of Preparation 3.

NMR (CDCl$_3$, δ):0.90 (d, 6H), 1.4–1.65 (m, 12H), 2.63 (s) and 2.65 (s) (3H), 3.05–3.15 (m, 2H), 3.77 (s, 3H), 4.65–4.75 (m) and 4.95–5.25 (m) (4H), 6.55 (bs, 1H), 7.08 (d, 2H), 7.2–7.4 (m, 7H)

IR (KBr):1735, 1695, 1685 cm$^{-1}$

Preparation 27

To a solution of Boc-MeLeu-D-p-CbmNHPhLac-OBzl (2.80 g) in methanol (25 ml) was added 10% palladium-charcoal (0.5 g) and ammoniumformate (0.63 g) under nitrogen atmosphere and the mixture was stirred at ambient temperature for 2 hours. The catalyst was filtered off and the filtrate was evaporated in vacuo. To the obtained residue was added water (100 ml) and 5% citric acid aqueous solution (50 ml) and extracted with ethyl acetate: (50 ml×2). The ethyl acetate layer was washed with 5% citric acid aqueous solution and brine successively, dried over anhydrous sodium sulfate and evaporated in vacuo to give Boc-MeLeu-D-p-CbmNHPhLac-Oh (2.13 g).

IR (KBr):1734, 1695, 1675 cm$^{-1}$

Preparation 28

Boc-MeLeu-D-p-CbmNHPhLac-OH (2.11 g) was used instead of Boc-MeLeu-D-Lac-OH. Except above matter, Boc-MeLeu-D-p-CbmNHPhLac-MeLeu-D-Lac-OBzl (3.29 g) was obtained according to a similar manner to that of Preparation 6.

NMR (CDCl$_3$, δ):0.85–0.95 (m, 12H), 1.4–1.7 (m, 18H), 2.77 (s), 2.83 (s) and 2.89 (s) (6H), 3.0–3.1 (m, 2H), 3.77 (s, 3H), 4.65–4.80 (m) and 4.9–5.5 (m) (6H), 6.59 (bs, 1H), 7.16 (d, 2H), 7.3–7.4 (m, 7H)

IR (KBr):1735 cm$^{-1}$

Preparation 29

Boc-MeLeu-D-p-CbmNHPhLac-MeLeu-D-Lac-OBzl (3.28 g) was used instead of Boc-MeLeu-D-p-CbmNHPhLac-OBzl. Except above matter, Boc-MeLeu-D-p-CbmNHPhLac-MeLeu-D-Lac-OH (2.81 g) was obtained according to a similar manner to that of Preparation 27.

IR (KBr):1735, 1696, 1671 cm$^{-1}$

Preparation 30

To a solution of Boc-MeLeu-D-Lac-MeLeu-D-Lac-OBzl (1.5 g) in methylene chloride (10 ml) was added trifluoroacetic acid (5 ml) and the mixture was stirred under ice-cooling for 1 hour. After the solvent was evaporated in vacuo, water (50 ml) and sodium bicarbonate was added successively to the residue until pH9. The mixture was extracted with ether (50 ml×3) and the ether layer was washed with brine, dried over anhydrous sodium sulfate and evaporated in vacuo to give H-MeLeu-D-Lac-MeLeu-D-Lac-OBzl (1.25 g).

IR (KBr):1738, 1665 cm$^{-1}$

Preparation 31

Boc-MeLeu-D-p-CbmNHPhLac-MeLeu-D-Lac-OH (2.81 g) was used instead of Boc-MeLeu-D-p-Me$_2$NPhLac-OH and H-MeLeu-D-Lac-MeLeu-D-Lac-OBzl (2.27 g) was used instead of H-MeLeu-D-Lac-MeLeu-D-Lac-MeLeu-D-Lac-OBzl. Except above matter, Boc-MeLeu-D-p-CbmNHPhLac-MeLeu-D-Lac-MeLeu-D-Lac-MeLeu-D-Lac-OBzl (4.75 g) was obtained according to a similar manner to that of Preparation 10.

NMR (CDCl$_3$, δ):0.8–1.05 (m, 24H), 1.15–1.8 (m, 30H), 2.75–3.15 (m, 14H), 3.77 (s, 3H), 4.4–4.5 (m), 4.65–4.75 (m) and 4.9–5.5 (m) (10 H), 6.60 (bs, 1H), 7.15–7.4 (m, 9H)

IR (KBr):1735, 1694, 1666 cm$^{-1}$

Preparation 32

Boc-MeLeu-D-p-CbmNHPhLac-MeLeu-D-Lac-MeLeu-D-Lac-MeLeu-D-Lac-OBzl (4.7 g) was used instead of Boc-MeLeu-D-p-CbmNHPhLac-OBzl. Except above matter, Boc-MeLeu-D-p-CbmNHPhLac-MeLeu-D-Lac-MeLeu-D-Lac-MeLeu-D-Lac-OH (4.37 g) was obtained according to a similar manner to that of Preparation 27.

IR (KBr): 1734, 1694, 1663 cm$^{-1}$

Preparation 33

Boc-MeLeu-D-p-CbmNHPhLac-MeLeu-D-Lac-MeLeu-D-Lac-MeLeu-D-Lac-OH (4.37 g) was used instead of Boc-MeLeu-D-p-NPhLac-OBzl. Except above matter, HCl.H-MeLeu-D-p-CbmNHPhLac-MeLeu-D-Lac-MeLeu-D-Lac-MeLeu-D-Lac-OH (4.08 g) was obtained according to a similar manner to that of Preparation 9.

IR (KBr):1742, 1647 cm$^{-1}$

EXAMPLE 1

To a solution of 2HCl.H-MeLeu-D-p-Me$_2$NPhLac-MeLeu-D-Lac-MeLeu-D-Lac-MeLeu-D-Lac-OH (0.60 g) in methylene chloride (122 ml) was added N-methylmorpholine (0.35 ml) and his (2-oxo-3-oxazolidinyl) phosphinic chloride (0.23 g) under ice-cooling and stirred for 15 hours.

The reaction mixture was evaporated in vacuo, and water (50 ml) was added and extracted with ethyl acetate (50 ml×3). The ethyl acetate layer was washed with brine, dried over anhydrous sodium sulfate and evaporated in vacuo. The resultant crude product was subjected to column chromatography on silica gel Muting with a mixture of hexane, ethyl acetate and ethanol (1:1:0.1 V/V). The fractions containing the desired product were combined and evaporated in vacuo give ⌐— MeLeu-D-p-Me$_2$NPhLac-MeLeu-D-Lac-MeLeu-D-Lac-MeLeu-D-Lac—┐
└────────────────────────────────────────────────────────────────────┘

(0.33 g).

NMR (CDCl$_3$, δ) 0.75–1.1 (m, 24H), 1.2–1.9 (m, 21H), 2.75–3.2 (m, 20H), 4.4–5.8 (m, 8H), 6.64 (d, 2H), 7.10 (d, 2H)

IR (KBr):1741, 1663 cm$^{-1}$ FAB-MS: 916[M+H]$^+$

EXAMPLE 2

The compound,

⎡— MeLeu-D-p-MorPhLac-MeLeu-D-Lac-MeLeu-D-Lac-MeLeu-D-Lac —⎤

(0.86 g) was obtained according to a similar manner to that of Example 1 by using 2HCl.H-MeLeu-D-p-MorPhLac-MeLeu-D-Lac-MeLeu-D-Lac-MeLeu-D-Lac-OH (1.66 g) instead of 2HCl.H-MeLeu-D-p-Me$_2$NPhLac-MeLeu-D-Lac-MeLeu-D-Lac-MeLeu-D-Lac-OH.

NMR (CDCl$_3$, δ) 0.75–1.1 (m, 2 4 H), 1.2–1.9 (m, 21H), 2.8–3.2 (m, 18H), 3.8–3.9 (m, 4H), 4.45–4.55 (m) and 5.0–5.7 (m) (8H), 6.82 (d, 2H), 7.13 (d, 2H)

IR (KBr):1741, 1663 cm$^{-1}$ FAB-MS 958[M+H]$^+$

EXAMPLE 3

The compound,

⎡— MeLeu-D-p-MeOPhLac-MeLeu-D-Lac-MeLeu-D-Lac-MeLeu-D-Lac —⎤

(0.422 g) was obtained according to a similar manner to that of Example 1 by using HCl.H-MeLeu-D-p-MeOPhLac-MeLeu-D-Lac-MeLeu-D-Lac-MeLeu-D-Lac-OH (0.80 g) instead of 2HCl.H-MeLeu-D-p-Me$_2$NPhLac-MeLeu-D-Lac-MeLeu-D-Lac-MeLeu-D-Lac-OH.

NMR (CDCl$_3$, δ) 0.75–1.1 (m, 24H), 1.2–2.0 (m, 21H), 2.8–3.2 (m, 14H), 3.78 (s, 3H), 4.45–4.55 (m) and 5.0–5.7 (m) (8H), 6.75–6.85 (m, 2H), 7.1–7.2 (m, 2H)

IR (KBr):1743, 1663 cm$^{-1}$ FAB-MS: 903[M+H]$^+$

EXAMPLE 4

To a solution of

⎡— MeLeu-D-PhLac-MeLeu-D-Lac-MeLeu-D-Lac-MeLeu-D-Lac —⎤

(59.5 mg) in methylene chloride was added fuming nitric acid (0.12 ml) under ice-cooling and stirred for 30 minutes at the same temperature.

The reaction solution was added gradually to saturated sodium bicarbonate aqueous solution (40 ml) and extracted with ethyl acetate (40 ml×3). The ethyl acetate layer was washed with brine, dried over anhydrous sodium sulfate and evaporated in vacuo to give crude product (62.9 g) of ⎡— MeLeu-D-p-NO$_2$PhLac-MeLeu-D-Lac-MeLeu-D-Lac-MeLeu-D-Lac —⎤

NMR (CDCl$_3$, δ) 0.75–1.1 (m, 24H), 1.2–2.0 (m, 21H), 2.75–3.3 (m, 14H), 4.45–4.55 (m) and 5.0–5.8 (m) (8H), 7.2–7.3 (m, 2H), 8.1–8.2 (m, 2H)

IR (KBr):1742, 1663 cm$^{-1}$ FAB-MS: 940[M+Na]$^+$

EXAMPLE 5

To a solution of crude product (53 mg) of

⎡— MeLeu-D-p-NO$_2$PhLac-MeLeu-D-Lac-MeLeu-D-Lac-MeLeu-D-Lac —⎤ in methanol (8 ml) was added 10% palladium-charcoal (0.03 g) and the mixture was subjected to hydrogenation reaction under hydrogen atmosphere (1 atm.) at ambient temperature for 4 hours. The catalyst was filtered off and the filtrate was evaporated in vacuo. The resultant crude product was subjected to column chromatography on silica gel eluting with a mixture of hexane, ethyl acetate and ethanol (60:35:5 V/V). The fractions containing the desired product were combined and evaporated in vacuo to give

```
┌─ MeLeu-D-p-NH2PhLac-MeLeu-D-Lac-MeLeu-D-Lac-MeLeu-D-Lac ─┐
│                                                         │
└─────────────────────────────────────────────────────────┘
```

(25 mg).

NMR (CDCl$_3$, δ) 0.8–1.1 (m, 24H), 1.15–1.95 (m, 21H), 2.7–3.15 (m, 14H), 4.45–4.55 (m) and 5.0–5.7 (m) (8H), 6.55–6.65 (m, 2H), 6.95–7.1 (m, 2H)

IN (KBr):1740, 1658 cm$^{-1}$ $^{FAB-MS}$:888[M+H]$^+$

EXAMPLE 6

A suspended solution of

```
┌─ MeLeu-D-p-NH2PhLac-MeLeu-D-Lac-MeLeu-D-Lac-MeLeu-D-Lac ─┐
│                                                         │
└─────────────────────────────────────────────────────────┘
```

(20 mg), bis (2-chloroethyl) ether (0.004 ml), potassium carbonate (9.4 mg) and sodium iodide (3.4 mg) in dimethylformamide (0.2 ml) was heated at 75° C. for 15.5 hours. After cooling down to room temperature, water (20 ml) was added and extracted with ethyl acetate (20 ml×3). The ethyl acetate layer was washed with brine, dried over anhydrous sodium sulfate and evaporated in vacuo. The resultant crude product was subjected to column chromatography on silica gel eluting with a mixture of hexane, ethyl acetate and ethanol (60:35:5 V/V). The fractions containing the desired product were combined and evaporated in vacuo to give

```
┌─ MeLeu-D-p-MorPhLac-MeLeu-D-Lac-MeLeu-D-Lac-MeLeu-D-Lac ─┐
│                                                         │
└─────────────────────────────────────────────────────────┘
```

(11.9 mg).

NMR (CDCl$_3$, δ) 0.75–1.1 (m, 9.4 H), 1.2–1.9 (m, 21H), 2.8–3.2 (m, 18H), 3.8–3.9 (m, 4H), 4.45–4.55 (m) and 5.0–5.7 (m) (8H), 6.82 (d, 2H), 7.13 (d, 2H)

IR (KBr):1741, 1663 cm$^{-1}$ FAB-MS: 958[M+H]$^+$

EXAMPLE 7

The compound,

```
┌─ MeLeu-D-p-CbmNH-PhLac-MeLeu-D-Lac-MeLeu-D-Lac-MeLeu-D-Lac ─┐
│                                                            │
└────────────────────────────────────────────────────────────┘
```

(1.76 g) was obtained according to a similar manner to that of Example 1 by using HCl.H-MeLeu-D-p-CbmNHPhLac-MeLeu-D-Lac-MeLeu-D-Lac-MeLeu-D-Lac-OH (4.08 g) was used instead of 2HCl.H-MeLeu-D-p-Me$_2$NPhLac-MeLeu-D-Lac-MeLeu-D-Lac-MeLeu-D-Lac-OH.

NMR (CDCl₃, δ):0.8–1.1 (m, 24H), 1.3–1.8 (m, 21H), 2.6–3.2 (m, 14H), 3.77 (s, 3H), 4.4–4.55 (m) and 5.0–5.75 (m) (8H), 6.55–6.8 (m, 1H), 7.15–7.20 (m, 2H), 7.25–7.4 (m, 2H)

IR (KBr):1741, 1663 cm⁻¹ $^{FAB-MS:}$968[M+Na]⁺

EXAMPLE 8

⎡— MeLeu-D-p-CbmNH-PhLac-MeLeu-D-Lac-MeLeu-D-Lac-MeLeu-D-Lac —⎤

(0.946 g) was added to 30% hydrogen bromide in acetic acid and the mixture was stirred at ambient temperature for 8 hours. After the solvent was evaporated in vacuo, water (50 ml) and ethyl acetate (25 ml) was added to the residue, neutralized with sodium bicarbonate. The ethyl acetate layer was separated and the aqueous layer was extracted with ethyl acetate (25 ml×2). The combined ethyl acetate layer was washed with 5% sodium bicarbonate aqueous solution (50 ml) and brine (50 ml×2) successively, dried over anhydrous sodium sulfate and evaporated in vacuo to give ⎡— MeLeu-D-p-NH₂PhLac-MeLeu-D-Lac-MeLeu-D-Lac-MeLeu-D-Lac —⎤

(0.92 g).

IR (KBr):1740, 1658 cm⁻¹

EXAMPLE 9

⎡— MeLeu-D-p-NH₂PhLac-MeLeu-D-Lac-MeLeu-D-Lac-MeLeu-D-Lac —⎤

(0.92 g) was used instead of benzyl (R)-3-(4-aminophenyl)-2-hydroxypropionate. Except above matter, ⎡— MeLeu-D-p-Me₂NPhLac-MeLeu-D-Lac-MeLeu-D-Lac-MeLeu-D-Lac —⎤

(0.71 g) was obtained according to a similar manner to that of Preparation 2.

NMR (CDCl₃, δ):0.75–1.1 (m, 24H), 1.2–1.9 (m, 21H), 2.75–3.2 (m, 20H)4.4–5.8 (m, 8H), 6.64 (d, 2H), 7.10 (d, 2H)

IR (KBr):1741, 1663 cm⁻¹ $^{FAB-MS:}$916[EM+H]⁺

EFFECT

The compounds of the present invention have strong activities against parasites in the alimentary canal and medicines which are also effective against parasites in the tissues were found.

What we claim is:

1. A compound of the general formula:

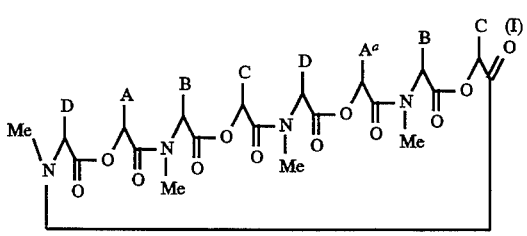

wherein A is a substituted benzyl group,

A^a, B and D are each lower alkyl, and

C is hydrogen or lower alkyl, or a salt thereof.

2. A compound of claim 1, wherein

A is a benzyl group substituted by cyclic amino, di-lower alkylamino or lower alkoxy, B and D are each isopropyl, and A^a and C are each methyl, or a salt thereof.

3. A compound of claim 1, wherein

A is a benzyl group substituted by morpholino, dimethylamino or methoxy, or a salt thereof.

4. A compound of claim 1, wherein

A is a benzyl group substituted by nitro, amino or protected amino,

B and D are each isopropyl, and $A^a$ and C are each methyl, or a salt thereof.

5. A compound of the formula:

[—MeLeu-D-p-Me₂NPhLac-MeLeu-D-Lac-MeLeu-D-Lac-MeLeu-D-Lac—]

or a salt thereof.

6. A compound of the formula:

[—MeLeu-D-p-MorPhLac-MeLeu-D-Lac-MeLeu-D-Lac-MeLeu-D-Lac—]

7. A compound of the formula:

[—MeLeu-D-p-MeOPhLac-MeLeu-D-Lac-MeLeu-D-Lac-MeLeu-D-Lac—]

8. A process for the preparation of a compound of the formula:

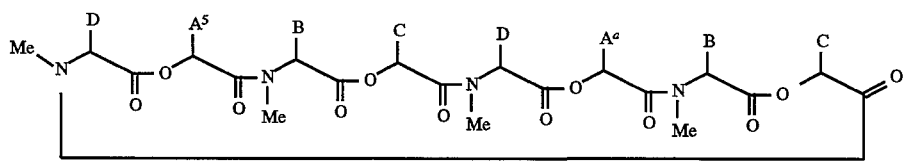

or a salt thereof, which comprises subjecting a compound of the formula:

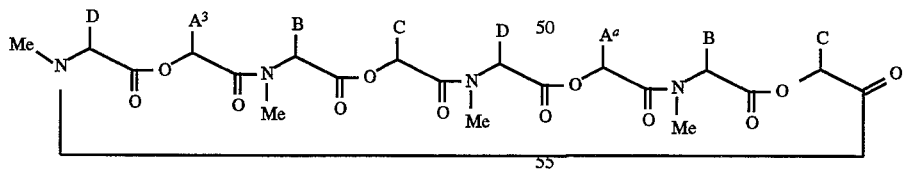

or a salt thereof to cyclic-alkylation, wherein

B and D are each lower alkyl, $A^a$ and C are each hydrogen or lower alkyl,

A3 is a benzyl group which has amino, or benzyl group which substituted by amino and lower alkoxy, A5 is a benzyl group substituted by cyclic amino, or a benzyl group substituted by cyclic amino and lower alkoxy.

9. A parasiticide which comprises, as an active ingredient, a compound of claim 1 or a salt thereof.

10. A compound of claim 1, wherein

A is a benzyl group substituted with a morpholino group,

B and D are each isobutyl, and $A^a$ and C are each methyl, or a salt thereof.

11. A compound of claim 1, wherein

A is a benzyl group substituted with a cyclic amino group,

B and D are each isobutyl, and $A^a$ and C are each methyl, or a salt thereof.

* * * * *